United States Patent [19]

Lee et al.

[11] Patent Number: 5,700,932
[45] Date of Patent: Dec. 23, 1997

[54] PROCESS FOR PREPARING CEPHEM DERIVATIVE

[75] Inventors: Kwang Hyuk Lee, Sungnam; Seung Sub Choi, Seoul; Myeong Sik Yoon, Kyungki-do, all of Rep. of Korea

[73] Assignee: Cheil Jedang Co., Seoul, Rep. of Korea

[21] Appl. No.: 719,068

[22] Filed: Sep. 24, 1996

[30] Foreign Application Priority Data

Jul. 19, 1996 [KR] Rep. of Korea .................. 96-29394

[51] Int. Cl.[6] ................................. C07D 513/04
[52] U.S. Cl. ................................... 540/223
[58] Field of Search ......................... 540/223

[56] References Cited

U.S. PATENT DOCUMENTS 4,472,574  9/1984  Hug .................................. 544/4

Primary Examiner—Robert T. Bond
Attorney, Agent, or Firm—Birch, Stewart, Kolasch & Birch, LLP

[57] ABSTRACT

The present invention relates to a process for preparing a cephem derivative represented by the following formula (I):

useful as an intermediate for the preparation of antibiotics.

5 Claims, No Drawings

PROCESS FOR PREPARING CEPHEM DERIVATIVE

BACKGROUND OF INVENTION

1. Field of Invention

The present invention relates to a process for preparing a cephem derivative represented by the following formula (I):

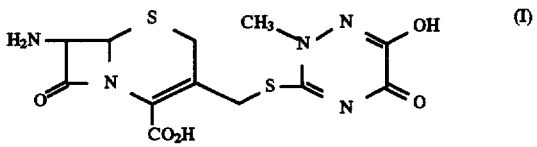

useful as an intermediate for the preparation of antibiotics.

(7R, 8R)-7-amino-3-[[(2,5-dihydro-6-hydroxy-2-methyl-5-oxo-as-triazin-3-yl)thio]methyl]-3-cephem-4-carboxylic acid of formula (I) above is an intermediate for the preparation of (7R, 8R)-7-[2-(amino-4-thiazolyl)-2-(Z-methoxyimino)-acetamido]-3-[[(2,5-dihydro-6-hydroxy-2-methyl-5-oxo-as-triazin-3-yl)thio]methyl]-3-cephem-4-carboxylic acid which is well known as an antibacterially-active cephem derivative.

2. Background Art

U.S. Pat. No. 4,472,574 discloses a process for preparing the cephem derivative of formula (I) above by reacting a compound represented by the following formula (II):

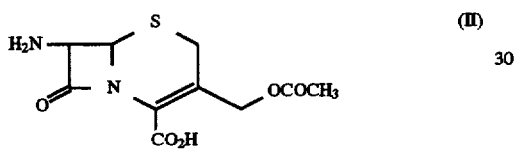

with a compound represented by the following formula (III):

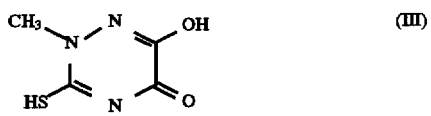

in the presence of boron trifluoride or a complex compound thereof in a polar organic solvent, and then adjusting the pH of the reaction solution to 1.6 to 1.8 with aqueous ammonia.

On the other hand, German Patent No. 2,804,896, which is opened to the public earlier than the above U.S. Patent, discloses another process for preparing the 7-amino-3-[5-(1-methyl-1,2,3,4-tetrazolyl)thiomethyl]-$\Delta^3$-cephem-4-carboxylic acid by reacting 7-aminocephalosporanic acid with 5-mercapto-1-methyl-1H-tetrazole in the presence of boron trifluoride or a complex compound thereof in a polar organic solvent, and then adjusting the pH of the reaction solution to 3.5 to 4.0 with an aqueous alkaline solution.

However, when the compound of formula (I) is crystallized by adjusting the pH to 3.5 to 4.0 with an aqueous alkaline solution in accordance with German Patent No. 2,804,896, the resulting compound contains a considerable amount of unidentified impurities (>10%); the time required for filtering the crystal thus obtained is increased; the silylation reaction of the compound of formula (I) with a silylating agent such as N,O-bis(trimethylsilyl)acetamide, trimethylsilylacetamide, trimethylchlorosilane or dimethyldichlorosilane in the presence of triethylamine is not carried out successfully; and as well the yield is low. Therefore, the inventors of the U.S. Patent method above tried to find out a method to solve the several problems as mentioned above. That is, it is described in the U.S. Patent specification that the problems of the German Patent method can be solved by adjusting the pH of the reaction solution to 1.6 to 1.8 with aqueous ammonia under a suitable solvent condition to crystallize the product.

However, the present inventors have found out that if an optimum solvent system is established in crystallization step of the compound of formula (I), the (7R,8R)-7-amino-3-[[(2,5-dihydro-6-hydroxy-2-methyl-5-oxo-as-triazin-3-yl)thio]methyl]-3-cephem-4-carboxylic acid of formula (I) can be prepared with a high purity (98.5% or more) and with a high yield though the crystallization is carried out at a pH of 3.5 to 3.7 as in the method of German Patent above, and then completed the present invention.

Specifically in the present method, contrary to the methods of prior arts, after the reaction of the compound of formula (II) with the compound of formula (III) is completed, the resulting crystal of the compound (I) is precipitated in a solvent system consisting of water and other organic solvent such as n-hexane besides acetonitrile at a pH range of 3.5 to 3.7 during separation and purification, thereby salts or impurities retained in the crystal are removed and as a result a highly pure crystal having an excellent crystal form can be obtained with a high yield.

DISCLOSURE OF INVENTION

Therefore, the present invention relates to a process for preparing a compound of the following formula (I):

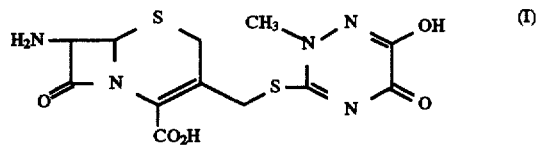

by reacting a compound of the following formula (II):

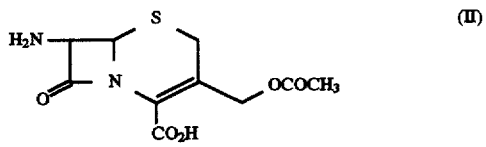

with a compound of the following formula (III):

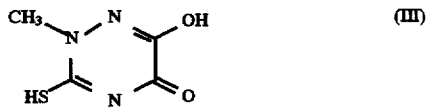

in the presence of boron trifluoride or a complex compound thereof in acetonitrile solvent, characterized in that the crystal of the compound of formula (I) is separated and purified by adding water and other organic solvent to the reaction mixture and adjusting the pH thereof to 3.5 to 3.7 with a base.

The compound of formula (I) prepared according to the process of the present invention reacts easily with a silylating agent such as N,O-bis(trimethylsilyl)acetamide, trimethylsilylacetamide, trimethylchlorosilane or dimethyldichlorosilane in the presence of trialkylamine such as triethylamine. In addition, it can be dissolved well in an organic solvent such as methylene-chloride, methanol or ethanol in the presence of triethylamine.

Hereinafter, the process according to the present invention is described more specifically.

As the "other organic solvent" used for precipitating the resulting compound of formula (I) as a crystal after reacting the (7R, 8R)-7-amino-cephalosporanic acid of formula (II) with the 2,5-dihydro-6-hydroxy-3-mercapto-2-methyl-5- oxo-as-triazine of formula (III), n-hexane, tolune, isopropanol, acetone and methanol can be mentioned. The composition ratio of the solvent mixture in the reaction solution may exert an important influence on purity, yield or crystal type of the product, or working conditions, etc. When n-hexane is used as other organic solvent in the present invention, it is preferable that composition ratio of acetonitrile: water: n-hexane is 1:0.7 to 1.5:0.2 to 0.7 by weight/volume and most preferable that the ratio thereof is 1:1:0.35 by weight/volume. In case the organic solvent such as toluene, isopropanol, acetone or methanol instead of n-hexane is used, preferable composition ratio of the solvent mixture is shown to have a similar range with n-hexane, however, purity of the product has been lowered because of poor filtration.

In addition, as the base used for adjusting the pH of the reaction solution to 3.5 to 3.7 in the present invention, one or more selected from a group consisting of ammonium hydroxide, sodium hydroxide and triethylamine can be mentioned, and among them sodium hydroxide is most preferable.

The present invention will be more specifically explained in the following examples. However, it should be understood that the following examples are intended to illustrate the present invention and not to limit the scope of the present invention in any manner.

EXAMPLE 1

100.0 ml of acetonitrile was introduced into a reaction vessel, cooled and then 9.3 g of boron trifluoride was added thereto. 7.0 g of 2,5-dihydro-6-hydroxy-3-mercapto-2-methyl-5-oxo-as-triazine and 10.0 g of 7-amino-cephalosporanic acid were successively added thereto and then the resulting solution was stirred for 30 minutes at 35° C. The reaction mixture was cooled to 10° C. or less, 74.0 ml of water and 35.0 ml of n-hexane were added thereto and then the solution was adjusted to pH 3.5 to 3.7 with 20%-aqueous sodium hydroxide solution at the same temperature. The resulting precipitate was washed successively with 60 ml of 50%-acetonitrile/water and 60 ml of acetone, filtered and dried under reduced pressure to obtain 11.2 g of substantially pure (7R, 8R) -7-amino-3-[[(2,5-dihydro-6-hydroxy-2-methyl-5-oxo-as-triazin-3-yl) thio]methyl]-3-cephem-4-carboxylic acid (yield: 82.1%).

Decomposition temperature: 201°–204° C.

Purity: 99.5%

EXAMPLE 2

100.0 ml of acetonitrile was introduced into a reaction vessel, cooled and then 25.5 g of ether complex of boron trifluoride was added thereto. 7.0 g of 2,5-dihydro-6-hydroxy-3-mercapto-2-methyl-5-oxo-as-triazine and 10.0 g of 7-amino-cephalosporanic acid were successively added thereto and then the resulting solution was stirred for 30 minutes at 50° C. The reaction mixture was cooled to 10° C. or less, 74.0 ml of water and 28.0 ml of n-hexane were added thereto and then the solution was adjusted to pH 3.5 to 3.7 with 20%-aqueous sodium hydroxide solution at the same temperature. The resulting precipitate was washed successively with 60 ml of 50%-acetonitrile/water and 60 ml of acetone, filtered and dried under reduced pressure to obtain 11.1 g of substantially pure (7R, 8R)-7-amino-3-[[(2,5-dihydro-6-hydroxy-2-methyl-5-oxo-as-triazin-3-yl)thio] methyl]-3-cephem-4-carboxylic acid (yield: 81.2%).

Decomposition temperature: 195°–199° C.

Purity: 98.8%

Comparative Example 1

In the present experiment, the solvents, which were used for separating and purifying the crystal of compound (I) from the reaction mixture in the above examples, were mixed and used in several different components and ratios from each other in order to determine how the components and ratio have an influence on the purity and yield of the compound of formula (I). The experimental results, yield, purity and working conditions, are summarized in the following Table 1.

TABLE 1

Effect of the solvent mixture depending on the components and ratio

| Lot No. | $CH_3CN$ | $H_2O$ | n-hexane | toluene | acetone | methanol | yield (%) | purity (%) | working condition |
|---|---|---|---|---|---|---|---|---|---|
| 1 | 1 | 1 | 0.20 | | | | 85.0 | 93.5 | B* |
| 2 | 1 | 1 | 0.35 | | | | 82.1 | 99.5 | A* |
| 3 | 1 | 1 | 0.50 | | | | 78.0 | 98.5 | A |
| 4 | 1 | 0.75 | 0.35 | | | | 82.0 | 98.3 | B |
| 5 | 1 | 1.25 | 0.35 | | | | 79.0 | 98.8 | A |
| 6 | 1 | 1 | | 0.35 | | | 86.0 | 91.0 | C* |
| 7 | 1 | 1 | | | 0.35 | | 86.2 | 93.1 | C |
| 8 | 1 | 1 | | | | 0.35 | 86.0 | 93.1 | C |

Note 1) Unit of the above values: Weight %
2) A: Filtration is good
B: Filtration is somewhat poor
C: Filtration is poor From the results described in Table 1, it is recognized that n-hexane is most preferable as the additionally used organic solvent, and that the most excellent effect can be obtained when the composition ratio of acetonitrile: water: n-hexane is 1:1:0.35 by weight/volume.

Accordingly, the present invention has accomplished a purpose for obtaining the crystal of compound (I) with good crystal form, high purity and high yield by a distinctive and inventive construction, i.e., by controlling the ratio of acetonitrile, water and other organic solvent such as n-hexane in the reaction mixture in a specific range and adjusting the pH thereof to 3.5 to 3.7 during separation and purification to precipitate the resulting crystal and remove the salts or impurities retained in the crystal.

Further, since the compound of formula (I) prepared according to the present invention easily reacts with a silylating agent in the presence of a trialkylamine and is satisfactorily dissolved in an organic solvent, it can be preferably used as an intermediate for the preparation of an antibacterially active compound.

What is claimed is:

1. A process for preparing a compound of the following formula (I):

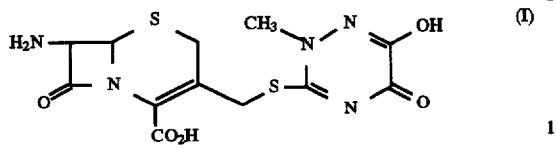

by reacting a compound of the following formula (II):

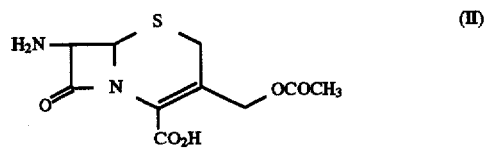

with a compound of the following formula (III):

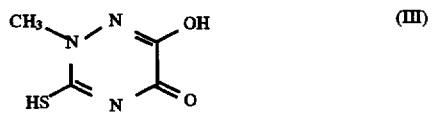

in the presence of boron trifluoride or a complex compound thereof in acetonitrile solvent, characterized in that the crystal of the compound of formula (I) is separated and purified by adding water and other organic solvent to the reaction mixture and adjusting the pH thereof to 3.5 to 3.7 with a base.

2. The process according to claim 1, characterized in that other organic solvent used is n-hexane, toluene, isopropanol, acetone or methanol.

3. The process according to claim 1, characterized in that the composition ratio of acetonitrile:water:other organic solvent is 1:0.7 to 1.5:0.2 to 0.7 by weight/volume.

4. The process according to claim 1, characterized in that the base is one or more selected from a group consisting of sodium hydroxide, triethylamine and ammonium hydroxide.

5. The process according to claim 2, characterized in that the composition ratio of acetonitrile:water:other organic solvent is 1:0.7 to 1.5:0.2 to 0.7 by weight/volume.

* * * * *